United States Patent [19]

Horstmann et al.

[11] Patent Number: 5,716,636
[45] Date of Patent: Feb. 10, 1998

[54] TRANSDERMAL THERAPEUTIC SYSTEM WITH ACETYLSALICYLIC ACID IN CRYSTALLINE FORM AS ACTIVE SUBSTANCE

[75] Inventors: Michael Horstmann, Neuwied; Gerd Hoffmann, Koblenz; Heinrich Kindel, Ehlscheid, all of Germany

[73] Assignee: LTS Lohmann Therapie-Systeme GmbH, Neuwied, Germany

[21] Appl. No.: 619,580

[22] PCT Filed: Sep. 16, 1994

[86] PCT No.: PCT/EP94/03106

§ 371 Date: Jul. 15, 1996

§ 102(e) Date: Jul. 15, 1996

[87] PCT Pub. No.: WO95/08330

PCT Pub. Date: Mar. 30, 1995

[30] Foreign Application Priority Data

Sep. 22, 1993 [DE] Germany ............ 43 32 093.7

[51] Int. Cl.⁶ ............................................. A61K 13/02
[52] U.S. Cl. ............................................. 424/448; 424/449
[58] Field of Search ............................................. 424/448, 449

[56] References Cited

U.S. PATENT DOCUMENTS

| | | | |
|---|---|---|---|
| 4,012,508 | 3/1977 | Burton | 424/235 |
| 4,228,162 | 10/1980 | Luzzi et al. | 424/232 |
| 4,286,592 | 9/1981 | Chandrasekaran | 128/260 |
| 4,460,368 | 7/1984 | Allison | 604/896 |
| 4,640,689 | 2/1987 | Sibalis | 604/20 |

FOREIGN PATENT DOCUMENTS

| | | | |
|---|---|---|---|
| 0156080 | 10/1985 | European Pat. Off. | A61L 15/06 |
| 4241128 | 6/1993 | Germany | A61L 15/44 |
| 31-12926 | 5/1991 | Japan . | |
| 88/10111 | 12/1988 | WIPO | A61K 9/70 |
| 92/14442 | 9/1992 | WIPO | A61K 9/10 |

OTHER PUBLICATIONS

Rougier et al., Journal of Pharmaceutical Sciences, vol. 76, No. 6, Jun., 1987, pp. 451–454.

Primary Examiner—D. Gabrielle Phelan
Attorney, Agent, or Firm—Wenderoth, Lind & Ponack

[57] ABSTRACT

Transdermal therapeutic system comprising the active substance acetylsalicylic acid, having a layered structure consisting of a backing layer which is substantially impermeable to active substances and moisture and one or several active substance-containing matrix layers, which is characterized in that at least one of said matrix layers comprises acetylsalicylic acid in mainly crystalline form.

11 Claims, 1 Drawing Sheet

TRANSDERMAL THERAPEUTIC SYSTEM WITH ACETYLSALICYLIC ACID IN CRYSTALLINE FORM AS ACTIVE SUBSTANCE

This application is a 371 of PCT/EP94/03106, filed Sep. 16, 1994.

The present invention relates to a transdermal therapeutic system for the release of acetylsalicylic acid and optional further substances via the skin to the human body. The system that will be described has an increased chemical hydrolytic stability for the active substance acetylsalicylic acid.

Transdermal therapeutic systems (TTS) have been established on the market in the medicinal therapy of various diseases.

BACKGROUND OF THE INVENTION

It is also known that the active substance acetylsalicylic acid has a basic permeativity through the human skin and is therefore suitable as a component in transdermal therapeutic systems. Rougier et al. (J. Pharm. Sci. Vol. 76, No. 6 451–454, 1987) have already described that the acetylsalicylic acid-absorption rate into the skin depends (to a rather small extent) on the chosen skin area. Chen et al. (Zhongguo Yiyuan Yaoxue Zazhi, Vol. 11, p. 245–247 (1991) give a report on a successful transdermal application of acetylsalicylic acid creams in children suffering from rheumatism.

JP 3 112 926 describes an agent for the percutaneous application, including acetylsalicylic acid, which agent is formed by dissolution in water and addition of water-swellable additives and is finally used in a silicone polymer in dispersed form. In this case, there is a great risk of hydrolysis due to the contact with water.

Acetylsalicylic acid has been introduced for some time and is a therapeutically effective drug having a high therapeutic index. Used in very high doses (more than one gram per day) it is used as an antirheumatic agent, in mean doses (250 to 500 mg) as an antipyretic/analgesic, and in a low dosage (30 to 150 mg per day) as a platelet aggregation inhibitor. Acetylsalicylic acid melts at a low temperature (about 139° C.) and is noticeably volatile at this temperature. Acetylsalicylic acid exists in several polymorphous forms (modifications) which partly melt at only 100° C. and also have different dissolution behavior.

Because of the unstable ester grouping it is susceptible to hydrolysis and transesterification. On the way to a stable administration form the following principles have to be observed in general:

- water, alcohols and esters as possible coreactants usually are unsuitable formulation components;
- for the same reason, in consideration of the law of mass action, it is useful to add potential reaction products, such as acetic acid or water-binding acetic anhydride as stabilizing components;
- since the hydrolysis proceeds slowest at a pH of about 2 to 3, adjustment to this acidity promotes stability;
- also, the use of additional stabilizing inactive ingredients is known, e.g., Luzzi and Ma (U.S. Pat. No. 4,228,162) recommend to use dimethylisosorbide as stabilizing solvent.

No indications have been found in literature as to how this galenic problem can be applied to the technique of manufacturing a TTS. First formulations wherein the TTS-matrix—following the state of the art—contained acetylsalicylic acid exclusively in dissolved form proved to be too unstable.

According to U.S. Pat. No. 4,286,592 a pharmaceutic active substance is used in crystalline form in a TTS in order to control the active substance release via an adhesive layer. A special ratio between the particle size of the crystals and the diffusion properties is important in this case. However, this application would only be used by those skilled in the art to limit an active substance flow but not for stabilization purposes with simultaneously maintaining the maximum possible release properties.

It is usual practice in some cases to load transdermal therapeutic systems with active substance to such a concentration that it crystallizes during the production after having been in complete solution initially (EP 0 156 080). By this a particularly long-lasting action is achieved. However, the method involves the disadvantage that it is difficult to control the procedure of crystallization and that, in the absence of crystal nuclei, modifications having a limited storage period are frequently obtained. Thus, the product cannot be manufactured to meet the required pharmaceutical quality. Indications as to stabilize active substances by introducing a high crystalline portion into transdermal therapeutic systems cannot be found in literature.

DESCRIPTION OF THE INVENTION

It is the object of the present invention to provide a transdermal therapeutic system with acetylsalicylic acid, which has a sufficient pharmaceutical stability at the maximum achievable release rate to the skin under the circumstances.

According to the present invention this object is achieved by a transdermal therapeutic system comprising the active substance acetylsalicylic acid and optional further substances and having a layered structure consisting of a backing layer which is substantially impermeable to active substances and moisture and one or several matrix layers, with at least one of said matrix layers comprising acetylsalicylic acid in mainly crystalline form.

Normally, an undesired limitation of the release properties in active substance crystals must be expected due to the fact that the dissolution rate could become lower than the permeation into the skin. Most surprisingly, this is not the case, if according to the present invention—in addition to careful drying of the layered components of the transdermal therapeutic system or other known stabilizing measures—a stabilizing phase of crystalline acetylsalicylic acid is formed prior to coating and drying. As a matter of fact, dry storage conditions are very useful to stabilize these properties since hydrolysis is repressed thereby. Such storage conditions can be ensured by gas and moisture resistant packing means and by insertion of one or more moisture-absorbing elements into the package.

The subject matter of the present invention will be illustrated in more detail in the following:

A characterizing and essential feature of the present invention is the presence of undissolved acetylsalicylic acid in a transdermal therapeutic system. In contrast to the prior art, at least a partial amount of the active substance employed prior to the drying process is maintained in an undissolved condition during the whole fabrication so that at least sufficient seed crystals of the stable active substance modification may come into the product. Thus, an only temporarily stable, oversaturated condition of the active substance solution—possibly under precipitation of metastable sediments—is avoided; this would involve high risks with respect to stability. In the course of time, uncontrolled recrystallizations will result in a product which no longer corresponds to the initial release rate specification.

The individual form of the present invention may vary within wide ranges. In the most simple case, the system of FIG. 1 corresponds to a single-layer matrix having pressure sensitive adhesive properties to the skin. The system consists of a backing layer which is substantially impermeable to the active substance, the matrix layer, and a removable protective layer which is to be removed prior to application.

Numerous substances standing out for a particular resistance and diffusion stability may be used as backing layer (1), among these polyester. But nearly any other plastics suitable for the application on the skin may be used, such as polyvinyl chloride, ethylene vinylacetate, vinyl acetate, polyethylene, polypropylene, cellulose derivatives, and many others. In particular cases an additional layer may be applied, e.g., by metallizing or vapor-plating with other additives forming a diffusion barrier, such as silicon dioxide, aluminum oxide, and the like. Also, for better acceptance, the outer side of the backing layer is frequently coated with a cuticolor varnish, or treated otherwise to improve the appearance. The thickness of the film-like backing layer normally amounts to 8 to 80 µm, depending—among others—on the stability and permeability of the chosen material; however, for special purposes it may also be thicker or thinner.

Among others, copolymers comprising acrylic esters, mixtures of rubbers and resins, polyvinyl acetate, silicone polymers and many other base materials compatible with the skin are suitable for the use as matrix layer (2) of the patch according to the present invention. The addition of up to 40% of fillers, such as titanium dioxide, zinc oxide, chalk, activated charcoal, finely divided silicon dioxide, etc. does by no means impair the function according to the present invention and may result in advantages with respect to the cohesion of the finished system.

The removable protective layer (3) is of less importance for the function; for instance, it may consist of a polyester material. However, any other plastics suitable for the application on the skin may be used, such as polyvinyl chloride, ethylene vinylacetate, vinyl acetate, polyethylene, polypropylene, cellulose derivatives, and many others. In particular cases metallizing or vapor-plating with other diffusion-blocking additives, such as silicon dioxide, aluminum oxide, and the like may be carried out. In any case, the surface facing the adhesive matrix must be treated with adhesive (release) materials, such as silicones or fluorine-containing plastics, so that the composite remains easily removable. The thickness of the film-like removable protective layer normally amounts to about 40 to 200 µm; for special purposes it may be thicker or thinner.

FIG. 2 shows as an additional embodiment of the present invention the arrangement in two matrix layers, which is also possible; the adhesive layer (4) advantageously comprises smaller and less numerous active substance crystals. By this an improved adhesion to the skin can be achieved, as compared to a single-layer system. With respect to the object of the present invention, it is not expedient to dispense completely with crystalline portions even in the adhesive layer, since the diffusion boundary layer could grow excessively wide, resulting in a reduced flow into the skin.

The size of the acetylsalicylic acid crystals is of no importance with respect to the function of the principle according to the present invention and to the basic advantage of stabilization as such. Smaller crystals having a diameter of below approximately 50 to 100 µm are advantageous, if only because of the more homogenous visual appearance. If extremely slightly dissolving matrix base materials, such as masses based on polyisobutylenes and larger crystal diameters (more than 300 µm) are used, a release control of the active substance through the skin may take place, involving the advantage that the release rate is controlled by the system, but involving the disadvantage that only part of the theoretically achievable flow rate can be achieved.

Independently of the construction of the system, volatile additives may be added, e.g., 2-pyrrolidone, benzyl alcohol, butanol and other short-chain alcohols, triglycerides, cholesterol, cineole, delta-tocopherol, diethyleneglycol, diethyleneglycol monoethylether, diisopropyl adipate, dimethyldecyl phosphoxide, dimethylisosorbide, dimethyllauroyl amide, dimethylsulfoxide, dodecylsulfoxide, acetic acid, ethyl acetate, and other aliphatic and aromatic esters, ethylene glycol, ethyleneglycol monolaurate, and other esters and ethers of ethylene glycol or propylene glycol, 2-octyl dodecanol, thin-bodied paraffin, glycerol, glycerol monooleate, glycerol monostearate, hydrogenated castor oil, isopropyl myristate, isopropyl palmitate, lauric acid diethanolamide, menthol or other volatile terpene derivatives (which are mixture components of many natural ethereal oils), methyl benzoate, methyloctylsulfoxide, mono- or diethylacetamide, N,N-diethyl-m-toluamide, N-methylpyrrolidone, 1-octanol and other volatile, medium-chain alcohols, octanoic acid and other medium-chain, aliphatic carboxylic acids, oleyl alcohol, olive oil, oleic acid, oleyl oleate, phenylethanol, propylene glycol, ricinoleic acid, triacetin, but also mixtures of these substances, e.g., oleic acid/propylene glycol. In special cases, however, the reactivity of the active substance acetylsalicylic acid with esters and acids as well as alcohols must be taken into consideration; this limits the use of such substances. However, the present invention limits the possible chemical reaction to the widest possible extent by means of compartments, thus it represents a stabilization advantage even in this respect.

In this connection, one alternative is of particular advantage; in this case the matrix layer is divided into two portions to be laminated onto each other, both comprising acetylsalicylic acid in mainly crystalline form according to the present invention; one of said portions comprises a highly volatile ingredient (e.g., one of the substances listed in the above paragraph), which remains in the system as a solvent for the residual components, and has been laminated with the second portion of the matrix layer during the production. Thus, after migration of the highly volatile component, a system having sufficient shear strength and comprising high-volatile additives can be obtained.

The acetylsalicylic acid content of the total matrix of the transdermal therapeutic system according to the present invention suitably amounts to about 15 to 60%-wt., preferably it is of the order of 35 to 50%-wt. In particular if readily dissolving matrix base materials are used, such as acrylic ester copolymers, exceeding the saturation solubility by factor 2 or even about 5 to 10 can only be achieved with such an extremely high load of the system with active substance.

It is useful for the system not only to stabilize the active substance against chemical degradation according to the present invention, but also to provide for a stabilization against physical ageing-influences.

This is easily possible with the structure described herein. To this effect, the thermodynamically most stable form of the acetylsalicylic acid, according to the latest knowledge that having a melting point of above 132° C. (depending on the degree of purity about 139° C.), is used in the manufacture, taking care in the production that always at least a small portion of the active substance, homogenously divided, remains in this original crystal modification.

In extreme cases, it is sufficient to prepare a saturated solution of acetylsalicylic acid and the pharmaceutical auxiliary agents of the matrix base, to disperse therein in crystalline form only about 1% of the acetylsalicylic acid in stable modification, to dry this mass, and to combine it with further sheets and/or matrix components.

Besides the solvent-based production processes it is also possible to use hot-melt methods to manufacture the matrix layer(s), however, in this case too, complete dissolution of the active substance particles must never occur during the process.

To sum it up it can be said that the present invention provides a TTS in which acetylsalicylic acid is present in undissolved form. The production of a stabilizing phase of crystalline acetylsalicylic acid makes possible a sufficient stability at a maximum release rate to the skin.

Figure 1:
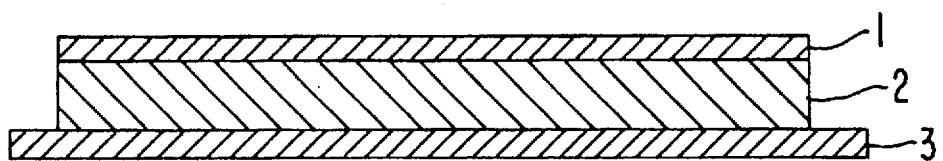
FIG. 1: System according to the present invention having a single-layer matrix
1. Backing layer which is impermeable to active substances
2. Matrix with dissolved and crystalline active substance portion
3. Removable protective layer.
Figure 2:
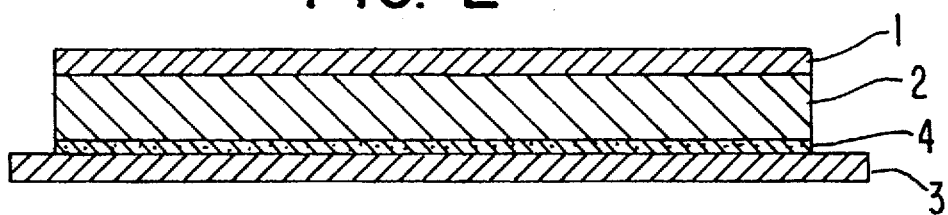
FIG. 2: System according to the present invention according to claim 3
1. Backing layer which is impermeable to active substances
2. Matrix with dissolved and crystalline active substance portion
3. Removable protective layer
4. Matrix layer ("adhesive layer") with smaller and less frequent acetylsalicylic acid crystals.
Figure 3:
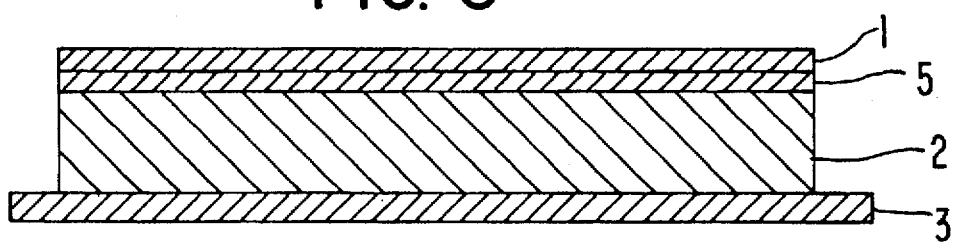
FIG. 3: System according to the present invention according to claim 4
1. Backing layer which is impermeable to active substances
2. Matrix with dissolved and crystalline active substance portion
3. Removable protective layer
4. Matrix layer remote from the skin with acetylsalicylic acid, consisting of a solution of the matrix components in a solvent remaining in the TTS.

We claim:

1. In a transdermal therapeutic system comprising the active substance acetylsalicylic acid, said system having a layered structure consisting of a backing layer which is substantially impermeable to active substances and moisture, and at least one active substance-containing matrix layer, the improvement wherein at least one of said matrix layers comprises greater than 50% of the acetylsalicylic acid in crystalline form.

2. A transdermal therapeutic system according to claim 1, wherein the acetylsalicylic acid is present as a stable, anhydrous modification, the crystalline form of which melts at a temperature above 132° C.

3. A transdermal therapeutic system according to claim 1, having two matrix layers, one of said layers facing the skin and being pressure sensitive adhesive, the matrix layer which is remote from the skin comprising anhydrous acetylsalicylic acid in crystalline form, and wherein the pressure sensitive adhesive matrix layer comprises a minor amount of acetylsalicylic acid crystals in order to maintain adhesive properties over the whole area of said matrix layer.

4. A transdermal therapeutic system according to claim 1 having two matrix layers, one of said layers facing the skin and being pressure sensitive adhesive, wherein both matrix layers comprise anhydrous acetylsalicylic acid in crystalline form and the matrix layer remote from the skin is produced from a solution of the matrix components in a solvent permanently remaining in the transdermal therapeutic system.

5. A transdermal therapeutic system according to claim 1 wherein the matrix layers and optionally the adhesive layer comprise as base material an acrylic ester copolymer.

6. A transdermal therapeutic system according to claim 1 wherein the portion of acetylsalicylic acid in the matrix material amounts to 15 to 60%-wt.

7. A transdermal therapeutic system according to claim 6 wherein the portion amounts to 35 to 50%-wt.

8. A transdermal therapeutic system according to claim 1 wherein the solvent in the matrix layers comprises permeation enhancers.

9. A process for the manufacture of a transdermal therapeutic system according to claim 1, wherein acetylsalicylic acid, in a suspension, solution or melt of the matrix base material, is applied in one layer to a film-like base material which has release properties and is then dried, subsequently covering the layer by applying a backing layer which is substantially impermeable to active substances and moisture, and subdividing the substrate by contour punching or film cutting.

10. A process according to claim 9, wherein single transdermal therapeutic systems are sealed in packages in a gas-tight manner such that the packing material withdraws moisture from the transdermal therapeutic system by water-absorption.

11. A process according to claim 9 wherein at least a portion of the active substance is maintained in undissolved condition during the fabrication so that a sufficient number of seed crystals of the stable active substance are present in the system.

* * * * *